(12) United States Patent
Doki et al.

(10) Patent No.: US 11,454,564 B2
(45) Date of Patent: Sep. 27, 2022

(54) GAS SENSOR FAULT DETECTION DEVICE, GAS SENSOR FAULT DETECTION SYSTEM, AND GAS SENSOR FAULT DETECTION METHOD

(71) Applicant: YAMAHA FINE TECHNOLOGIES CO., LTD., Hamamatsu (JP)

(72) Inventors: Yuichi Doki, Hamamatsu (JP); Takeshi Kato, Shimada (JP)

(73) Assignee: YAMAHA FINE TECHNOLOGIES CO., LTD., Hamamatsu (JP)

( * ) Notice: Subject to any disclaimer, the term of this patent is extended or adjusted under 35 U.S.C. 154(b) by 40 days.

(21) Appl. No.: 16/750,808

(22) Filed: Jan. 23, 2020

(65) Prior Publication Data

US 2020/0158593 A1  May 21, 2020

Related U.S. Application Data

(63) Continuation of application No. PCT/JP2018/026189, filed on Jul. 11, 2018.

(30) Foreign Application Priority Data

Jul. 28, 2017  (JP) .............................. JP2017-147130

(51) Int. Cl.
*G01M 3/22* (2006.01)
*G01N 33/00* (2006.01)

(52) U.S. Cl.
CPC .......... *G01M 3/227* (2013.01); *G01N 33/007* (2013.01)

(58) Field of Classification Search
CPC .......... G01M 3/20; G01M 3/22; G01M 3/227; G01M 3/007; G01M 3/207
See application file for complete search history.

(56) References Cited

U.S. PATENT DOCUMENTS

| 4,492,110 A | * | 1/1985 | Bergquist | .............. G01M 3/207 250/288 |
| 4,991,426 A | * | 2/1991 | Evans | ..................... G01M 3/24 73/1.05 |
| 5,719,785 A | * | 2/1998 | Standifer | .............. G01M 3/243 702/140 |

(Continued)

FOREIGN PATENT DOCUMENTS

| CN | 105203261 A | 12/2015 |
| JP | S58106741 U | 7/1983 |

(Continued)

OTHER PUBLICATIONS

Office Action issued in Chinese Appln. No. 201880049573.X dated Apr. 19, 2021. English translation provided.

(Continued)

*Primary Examiner* — Erika J. Villaluna
(74) *Attorney, Agent, or Firm* — Rossi, Kimms & McDowell LLP

(57) ABSTRACT

There is provided a gas sensor fault detection device that detects a sensor fault in a gas leak inspection device. The gas sensor fault detection device includes: a gas blowing unit that blows a gas toward a detection area of a gas sensor of the gas leak inspection device; and a position fixing unit that fixes a position of the gas blowing unit with reference to a hypothetical gas leak position of an inspection target being inspected by the gas leak inspection device.

6 Claims, 5 Drawing Sheets

(56) References Cited

U.S. PATENT DOCUMENTS 6,332,350 B1    12/2001    Inoue

FOREIGN PATENT DOCUMENTS

| | | | |
|---|---|---|---|
| JP | S62175639 A | | 8/1987 |
| JP | 2000074778 A | | 3/2000 |
| JP | 2006145252 A | * | 6/2006 |
| JP | 2013194639 A | * | 9/2013 |
| KR | 2020160001146 U | | 4/2016 |

OTHER PUBLICATIONS

Office Action issued in Korean Appln. No. 10-2020-7001268 dated Jul. 6, 2021. English machine translation provided.
International Search Report issued in Intl. Appln. No PCT/JP2018/026189 dated Sep. 11, 2018. English translation provided.
Written Opinion issued in Intl. Appln. No. PCT/JP2018/026189 dated Sep. 11, 2018.
Yamaha Fine Technologies Co., Ltd. "Helium Leak Tester." Retrieved on Jul. 24, 2017. English translation provided. Cited in specification.
Office Action issued in Chinese Appln. No. 201880049573.X dated Dec. 27, 2021. English machine translation provided.
Office Action issued in Chinese Appln. No. 201880049573.X dated May 23, 2022. English machine translation provided.

* cited by examiner

GAS SENSOR FAULT DETECTION DEVICE, GAS SENSOR FAULT DETECTION SYSTEM, AND GAS SENSOR FAULT DETECTION METHOD

CROSS-REFERENCE TO RELATED APPLICATIONS

The present application is a continuation application of International Application No. PCT/JP2018/026189, filed Jul. 11, 2018, which claims priority to Japanese Patent Application No. 2017-147130, filed Jul. 28, 2017. The contents of these applications are incorporated herein by reference.

BACKGROUND OF THE INVENTION

Field of the Invention

The present invention relates to a gas sensor fault detection device, a gas sensor fault detection system, and a gas sensor fault detection method.

Description of Related Art

Conventionally, there is a gas leak inspection device that inspects whether or not a gas that fills a hollow object (inspection target) is leaking from the inspection target to the outside. Yamaha Fine Technologies Co., Ltd. Home Page, Helium Leak Tester Leak Detection System [online] [searched Jul. 24, 2017], Internet <URL: www.yamahafinetech.co.jp/products/leaktester/he_leaktester/pdf/leaktester_catalog001.pdf>, hereinafter referred to as Non-Patent Document 1, discloses a leak tester for an aluminum wheel, a leak tester for a drum can, a fuel tank-dedicated leak inspection device for a vehicle, and the like.

The gas leak inspection devices (leak testers) described in Non-Patent Document 1 above are provided with a gas sensor that detects leaked gas. When a fault occurs in the gas sensor, gas leak inspections cannot be performed with a high accuracy, and therefore, diagnosis of the fault with respect to the gas sensor is performed. In a fault diagnosis of a gas sensor, for example, a hole is made in an aluminum wheel representing a workpiece, to cause a gas to leak from the workpiece, and the diagnosis is performed based on whether or not the leaked gas is detected.

SUMMARY OF THE INVENTION

However, the fault diagnosis of a gas sensor described above simply makes a hole in the workpiece to cause the gas to leak from the workpiece. As a result, it is difficult to support gas leak inspections in anticipation of various cases, such as cases where there is a difference in the size of the workpiece, or in the leakage amount of the gas which is leaking from the workpiece.

The present invention has been made in view of the points described above. An exemplary object of the present invention is to provide a gas sensor fault detection device, a gas sensor fault detection system, and a gas sensor fault detection method capable of supporting gas leak inspections in anticipation of various cases.

A gas sensor fault detection device according to an aspect of the present invention is a gas sensor fault detection device that detects a sensor fault in a gas leak inspection device. The gas sensor fault detection device includes: a gas blowing unit that blows a gas toward a detection area of a gas sensor of the gas leak inspection device; and a position fixing unit that fixes a position of the gas blowing unit with reference to a hypothetical gas leak position of an inspection target being inspected by the gas leak inspection device.

A gas sensor fault detection system according to an aspect of the present invention includes: a gas sensor fault detection device that detects a sensor fault in a gas leak inspection device. The gas sensor fault detection device includes: a gas blowing unit that blows a gas toward a detection area of a gas sensor of the gas leak inspection device; and a position fixing unit that fixes a position of the gas blowing unit with reference to a hypothetical gas leak position of an inspection target being inspected by the gas leak inspection device; a gas sensor that detects the gas blown from the gas blowing unit of the gas sensor fault detection device; and a determination unit that determines whether there is a fault in the gas sensor based on a detection result from the gas sensor.

A gas sensor fault detection method according to an aspect of the present invention is a gas sensor fault detection method that detects a sensor fault in a gas leak inspection device. The gas sensor fault detection method includes: fixing a position of a gas blowing unit with reference to a hypothetical gas leak position of an inspection target being inspected by the gas leak inspection device; blowing a gas from the gas blowing unit toward a detection area of a gas sensor of the gas leak inspection device; detecting, by the gas sensor, the gas blown from the gas blowing unit; and determining whether there is a fault in the gas sensor based on a detection result from the gas sensor.

EMBODIMENTS FOR CARRYING OUT THE INVENTION

First Embodiment

Figure 1:
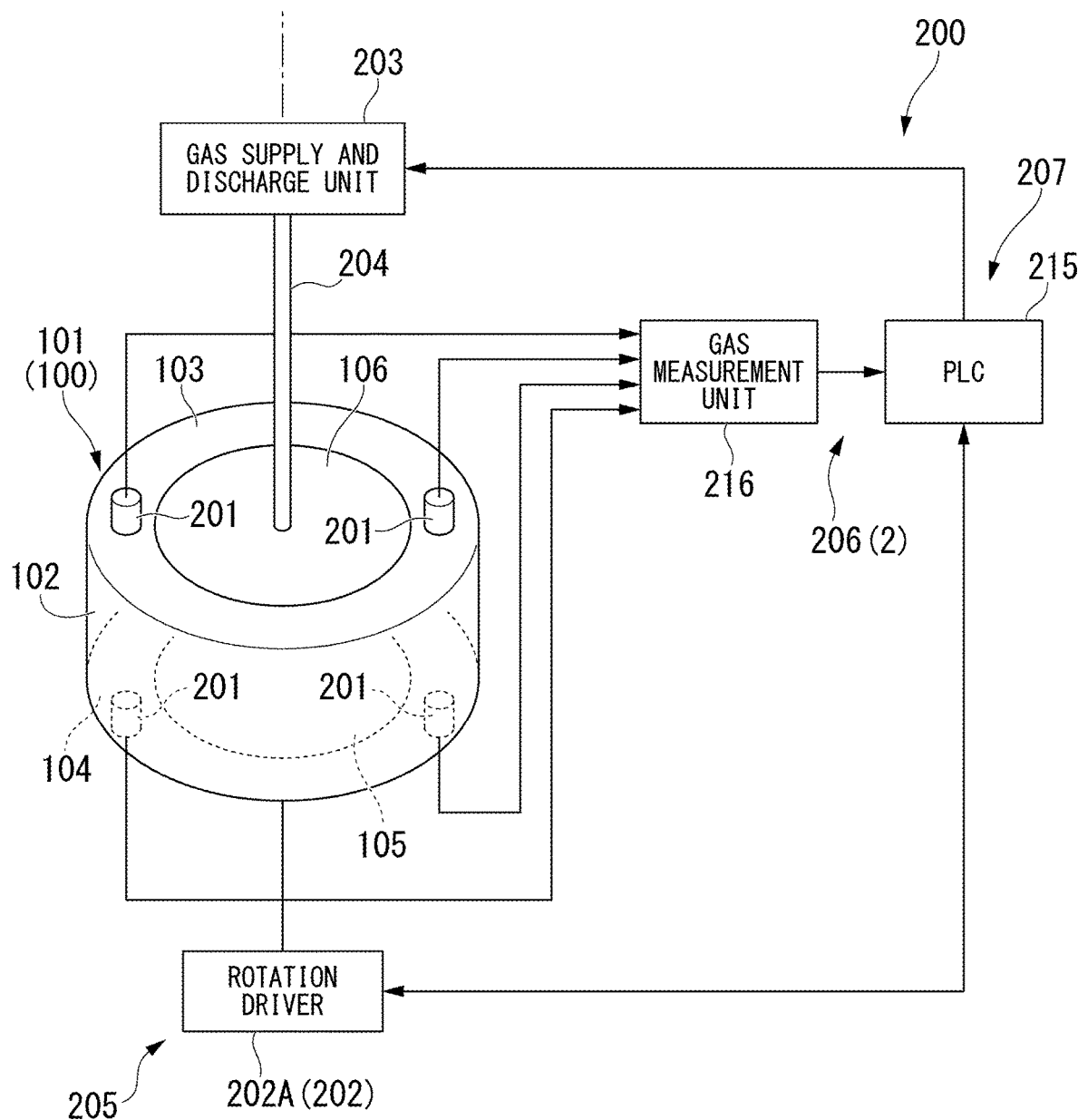
FIG. 1 is a diagram showing a configuration of a gas leak inspection device representing a fault detection target.

Hereunder, a first embodiment of the present invention will be described with reference to FIG. 1 and FIG. 2. In the following drawings, the thicknesses and dimensional ratios of the components are adjusted to make the drawings easier to see. In particular, in FIG. 3, the orifice section is drawn considerably larger than the actual dimensional ratio in order to make the orifice easier to see.

The gas sensor fault detection device of the first embodiment is a device that detects a fault in a gas sensor of a gas leak inspection device. The gas leak inspection device is a device that detects whether or not a gas leak has occurred from an inspection target, such as a tire. Therefore, before describing the gas sensor fault detection device, the configuration of the gas leak inspection device will be firstly described.

In the gas leak inspection device, the inspection target representing the gas leak inspection target is arbitrary. As shown in FIG. 1, the inspection target 100, which is the gas leak inspection target of the gas leak inspection device, is an axisymmetric object having an axisymmetric outer surface. Specifically, the inspection target 100 of the first embodiment is a tire 101 used in a vehicle, or the like. The tire 101 has, as an axisymmetric outer surface, a ground contact surface 102, and side surfaces 103 and 104. The ground contact surface 102 has a cylindrical shape, and extends along the axis of the tire 101. The side surfaces 103 and 104 have an annular shape, and are connected to both axial direction sides of the ground contact surface 102 so as to intersect the axis (for example, orthogonally). The side surfaces 103 and 104 of the tire 101 may, for example, be formed flat or curved. Both axial direction sides of the tire 101 are open. Consequently, when the tire 101 is inspected for a gas leak, the tire 101 is configured as a hollow inspection target by closing the openings at both sides of the tire 101 with a pair of lid portions 105 and 106.

The gas that fills the tire 101 at the time of a gas leak inspection (hereunder, also referred to as a "trace gas") may be any type of gas (reactive gas) that reacts with the gas sensor, such as hydrogen gas, helium gas, argon gas, or carbon dioxide gas. Furthermore, the trace gas may also be a mixed gas that includes the reactive gas (for example, a mixed gas of 5% hydrogen gas and 95% nitrogen). For example, a gas having a low viscosity (for example, a gas having a lower viscosity than the air injected into the tire 101 during use) may be selected as the trace gas.

Figure 2:
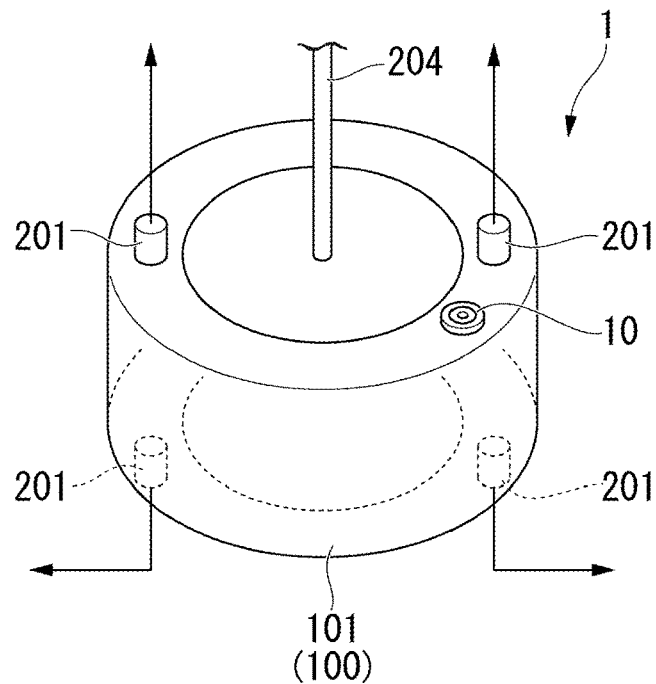
FIG. 2 is a diagram showing a configuration of gas sensor fault detection device.

As shown in FIG. 1, the gas leak inspection device 200 includes gas sensors 201 and a movement device (movement unit) 202. The gas sensors 201 are disposed facing the outer surface of the tire 101. The gas sensors 201 may be disposed close to the outer surface of the tire 101, in an area in which contact does not occur with the outer surface of the tire 101 (the ground contact surface 102 and the side surfaces 103 and 104). The gas sensors 201 detect the gas that fills the tire 101, outside of the tire 101. The gas sensors 201 detect the trace gas described above. The gas sensors 201 output the detected concentration of the trace gas as an electric signal (for example, as a voltage value).

The movement device 202 relatively moves the tire 101 and the gas sensors 201 so that the gas sensors 201 move along the outer surface of the tire 101. The movement device 202 relatively moves the tire 101 and the gas sensors 201 so that the distance from the outer surface of the tire 101 to the gas sensors 201 is kept constant. The relative moving direction and the like of the tire 101 and the gas sensors 201 caused by the movement device 202 is arbitrary. The movement device 202 relatively moves the tire 101 and the gas sensors 201 with the axis of the tire 101 serving as the center.

The movement device 202 may, for example, move the gas sensors 201 along the outer surface of the tire 101. In this case, the movement device 202 may include, for example, a robot arm that moves the gas sensors 201, and a computer that controls the robot arm so that the gas sensors 201 move according to the shape of the outer surface of the tire 101. When the tire 101 and the gas sensors 201 are relatively moved, both the tire 101 and the gas sensors 201 may be moved. The movement device 202 moves the tire 101 so that the gas sensors 201 move along the outer surface of the tire 101. More specifically, the movement device 202 is configured by a rotation driver 202A that rotates the tire 101 about its axis. The specific configuration of the rotation driver 202A is arbitrary. The rotation driver 202A is configured by a stepping motor capable of recognizing the rotational position of the tire 101.

The rotation driver 202A may, for example, be connected to a base on which the tire 101 is placed. The rotation driver 202A is connected to a first lid portion 105 that closes an opening of the tire 101. Because the rotation driver 202A is connected to the lid portion 105, the axis of the tire 101 and the axis of the rotation driver 202A can be easily matched.

The gas sensors 201 may be disposed so as to face at least a portion of the circumferential direction area of the outer surface of the tire 101. The gas sensors 201 may be disposed, for example, so as to face the ground contact surface 102 of the tire 101. The gas sensors 201 are disposed so as to face the side surfaces 103 and 104 of the tire 101. The number of gas sensors 201 is, for example, more than one, but may also be one.

The plurality of gas sensors 201 are arranged about the axis of the tire 101 with a spacing in the circumferential direction of the tire 101. Although the plurality of gas sensors 201 are arranged, for example, with an equal spacing in the circumferential direction of the tire 101, an arrangement with an unequal spacing in the circumferential direction of the tire 101 is also possible. In the example of FIG. 1, two gas sensors 201 are arranged in the circumferential direction of the tire 101.

Although the gas sensors 201 are disposed, for example, facing the side surfaces 103 and 104 on both sides of the tire 101, they may also be disposed facing only one side surface 103 of the tire 101. The position of the gas sensor 201 facing the one side surface 103 and the position of the gas sensor 201 facing the other side surface 104 coincide with each other, for example, in the radial direction or the circumferential direction of the tire 101. The position of the gas sensor 201 facing the one side surface 103 and the position of the gas sensor 201 facing the other side surface 104 may be mutually offset in the radial direction or circumferential direction of the tire 101.

Although the gas sensors 201 do not move, they may also move, for example, along the outer surface of the tire 101. Although the tire 101 does not move, it may also move. The tire 101 may move, for example, by rotating about its axis. As described above, the gas sensors 201 and/or the tire 101 may move so that the gas sensors 201 face one of the outer surfaces of the tire 101.

If the gas sensors 201 are disposed facing the side surfaces 103 and 104 of the tire 101, the gas sensors 201 may move in the radial direction of the tire 101. For example, if the gas sensors 201 are disposed facing the ground contact surface 102 of the tire 101, the gas sensors 201 may move in the axial direction of the tire 101. Furthermore, the plurality of gas sensors 201 may be arranged, for example, in a direction orthogonal to the movement direction of the outer surface of the tire 101 (for example, the radial direction or axial direction of the tire 101).

The gas leak inspection device 200 includes a gas supply and discharge unit 203. The gas supply and discharge unit 203 includes a gas supplier that supplies the trace gas to the inside of the tire 101. Furthermore, the gas supply and discharge unit 203 includes a gas discharger that discharges the trace gas from the inside of the tire 101. The supply and discharge of the gas with respect to the tire 101 by the gas supply and discharge unit 203 is controlled by a PLC 215 described below. The gas supply and discharge unit 203 is configured by appropriately combining, for example, a supply source of the trace gas (for example, a gas cylinder), a gas supply pipe that connects the supply source to the inside of the tire 101, a gas discharge pipe that connects the inside of the tire 101 to the outside, and valves provided in the middle of the pipes that switch between flowing the gas through the pipes and shutting off the flow (none of these are shown in the drawing). In the example shown in FIG. 1, a pipe 204 of the gas supply and discharge unit 203 is connected to a second lid portion 106 that closes the opening of the tire 101. The pipe 204 of the gas supply and discharge unit 203 serves as both the gas supply pipe and the gas discharge pipe.

The gas leak inspection device 200 includes a position detection device (position detection unit) 205, a determination device (determination unit) 206, and a leak position specification device (leak position specification unit) 207. The position detection device 205 detects the positions of the gas sensors 201 on the outer surface of the tire 101 based on a relative movement time or movement distance of the tire 101 and the gas sensors 201 caused by the movement device 202. The position detection device 205 detects the positions of the gas sensors 201 in the circumferential direction of the tire 101. Furthermore, if the gas sensors 201 move in the radial direction or axial direction of the tire 101, the position detection device 205 may detect, for example, the positions of the gas sensors 201 in the radial direction or axial direction of the tire 101. The position detection device 205 detects the positions of each of the plurality of gas sensors 201.

The position detection device 205 is configured by a PLC (Programmable Logic Controller) 215 and a rotation driver 202A. The PLC 215 is configured as a controller that controls the various operations of the gas leak inspection device 200, and a data management unit that manages the various data required by the gas leak inspection device 200. The PLC 215 detects the positions of the gas sensors 201 on the outer surface of the tire 101 based on data relating to the rotational position of the tire 101 sent from the rotation driver 202A. Furthermore, the PLC 215 also controls the operation of the rotation driver 202A (driving, stopping, speed adjustment, and the like).

The determination device 206 determines whether or not a gas leak has occurred in the tire 101 based on the concentration of the trace gas detected by the gas sensors 201. The determination device 206 determines that "a gas leak has not occurred in the tire 101 (there are no defects such as holes in the tire 101)" if the concentration of the trace gas detected by the gas sensors 201 is less than or equal to (or less than) a predetermined gas leak determination threshold. Furthermore, the determination device 206 determines that "a gas leak has occurred in the tire 101 (there is a defect such as a hole in the tire 101)" if the concentration of the trace gas detected by the gas sensors 201 is greater than or equal to the predetermined gas leak determination threshold.

The determination device 206 is configured by the PLC 215 and a gas measurement unit 216. The gas measurement unit 216 is connected to the gas sensors 201. The gas measurement unit 216 converts an electric signal (voltage value) output from each gas sensor 201 into a concentration of the trace gas. The reference data for converting an electrical signal (voltage value) into a concentration of the trace gas may be stored, for example, in the gas measurement unit 216. In the present example, the reference data is stored in the PLC 215. Consequently, when an electrical signal is converted into a concentration of the trace gas in the gas measurement unit 216, the reference data described above is sent from the PLC 215 to the gas measurement unit 216. The concentrations of the trace gas (or voltage values) converted in the gas measurement unit 216 are sent to the PLC 215 in a state where they are associated with each gas sensor 201.

The PLC 215 stores data relating to the gas leak determination threshold for determining whether or not a gas leak has occurred in the tire 101. The gas leak determination threshold may be a concentration of the trace gas, or may be a voltage value. The PLC 215 compares the concentration of the trace gas (or voltage value) sent from the gas measurement unit 216 with the gas leak determination threshold described above, and determines whether or not a gas leak has occurred in the tire 101 based on the comparison result. The gas measurement unit 216 may include, for example, a display that displays the concentration of the trace gas. The display of the gas measurement unit 216 may display, for example, the voltage values output from the gas sensors 201.

A case where the determination device 206 determines that "a gas leak has occurred in the tire 101" will be described. In this case, the leak position specification device 207 associates the positions of the gas sensors 201 detected by the position detection device 205 (positions of the gas sensors 201 with respect to the outer surface of the tire 101) and the concentrations of the trace gas detected by the gas sensors 201, and specifies the position where the gas leak has occurred in the tire 101 based on the correspondence thereof. The leak position specification device 207 is configured by the PLC 215.

The PLC 215 associates the positions of the gas sensors 201 with the concentrations of the trace gas detected by the gas sensors 201, irrespective of the presence of a gas leak. The associated data is sent to a PC (personal computer) (not shown in the drawing), and is stored in a storage of the PC, or is displayed on a display of the PC. Data that specifies the inspected tire 101 (for example, an identification number) may be associated with the associated data described above.

A gas leak inspection method using the gas leak inspection device 200 is performed according to the following procedure. First, the PLC 215 rotates the rotation driver 202A so as to rotate the tire 101 about its axis. Consequently, the gas sensors 201 relatively move along the outer surface of the tire 101. Furthermore, the PLC 215 supplies the trace gas from the gas supply and discharge unit 203 to the tire 101. Then, the gas sensors 201 detect the trace gas, and output electric signals (voltage values) to the PLC 215 that correspond to the detected concentrations of the trace gas. The PLC 215 determines whether or not a gas leak has occurred in the tire 101 based on the output electric signals. At this time, the PLC 215 recognizes the rotational position of the rotation driver 202A, which corresponds to the position of the tire 101 from which gas is determined to be leaked. Consequently, if the gas is leaking from the tire 101, the gas leak inspection device 200 is capable of specifying the gas leak position (gas leak area) at least in the circumferential direction of the tire 101.

Next, a gas sensor fault detection system of the first embodiment will be described. As shown in FIG. 2, the gas sensor fault detection system includes a gas sensor fault detection device 1 and a determination unit 2 (see FIG. 1). In the gas sensor fault detection system, the rotation driver 202A, the gas supply and discharge unit 203, the PLC 215, and the gas measurement unit 216 and the like of the gas leak inspection device 200 shown in FIG. 1 are used as is.

Figure 3:
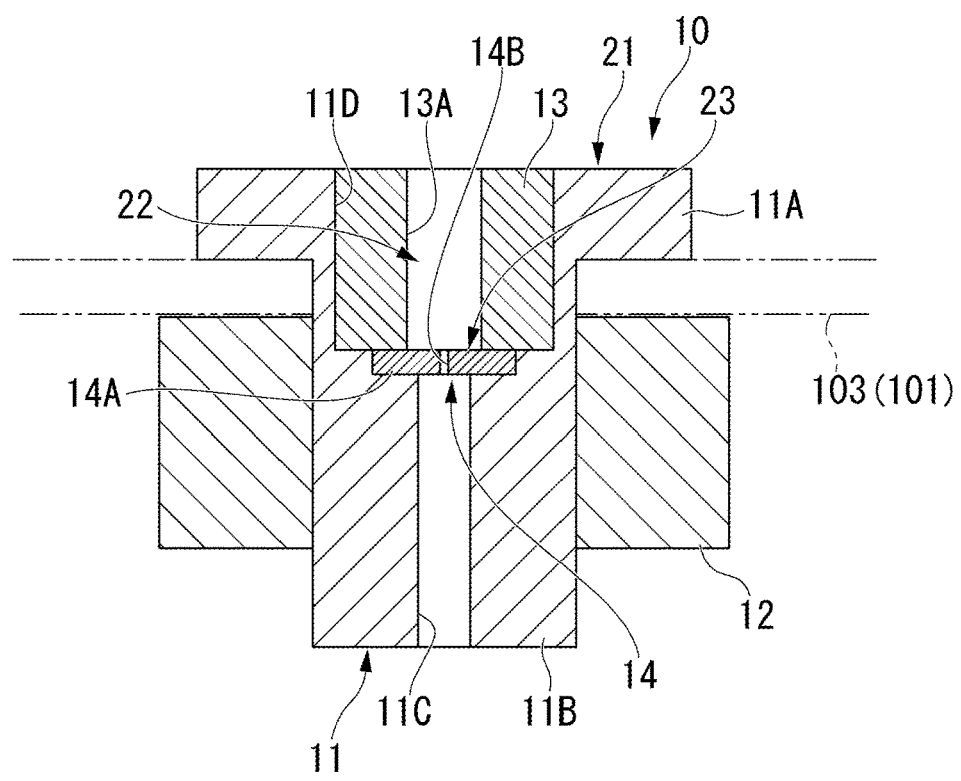
FIG. 3 is a cross-sectional view of an installation jig.

As shown in FIG. 3, the gas sensor fault detection device 1 includes a position fixing unit 21, a gas blowing unit 22, and a blowing amount adjustment unit 23. The gas sensor fault detection device 1 is configured by an installation jig 10. The position fixing unit 21 fixes the position of the gas blowing unit 22. The gas blowing unit 22 blows out the trace gas that fills the tire 101. The blowing amount adjustment unit 23 adjusts the blowing amount of the trace gas that blows out from the gas blowing unit 22. The position fixing unit 21 is configured by a holder portion 11, a nut 12, and a securing screw 13. The gas blowing unit 22 is configured by a blowing outlet 13A, from which the trace gas blows out. The blowing amount adjustment unit 23 is configured by an orifice portion 14.

The installation jig 10, for example, is installed such that it penetrates one side surface 103 of the tire 101. The installation jig 10 is disposed at a hypothetical gas leak position, where a gas leak in the tire 101 is anticipated to occur. In the example shown in FIG. 2, one installation jig 10 is installed on the tire 101, but it is not limited to such an example. A plurality of installation jigs 10 that corresponds to the number of gas sensors 201 may be installed on the tire 101. For example, the installation jig 10 may be installed on one of the side surfaces 103 and 104 of the tire 101, or may be installed on both. For example, the trace gas constantly blows out from the installation jig 10. Furthermore, the tire 101 is rotated by the rotation driver 202A. Therefore, the trace gas that blows out from the installation jig 10 blows out toward the detection areas of the gas sensors 201 when the installation jig 10 passes predetermined positions, for example, positions which are directly below or in the vicinity of the gas sensors 201. The installation jig 10 may blow out the trace gas in accordance with the timings in which the installation jig 10 passes directly below the gas sensors 201. Therefore, the trace gas may be blown out only during periods that extend from before until after the installation jig 10 passes directly below the gas sensors 201.

As shown in FIG. 3, the installation jig 10 includes a holder portion 11, a nut 12, a securing screw 13, and an orifice portion 14. The cross-section of the holder portion 11 is substantially letter-T shaped. The holder portion 11 includes a top plate portion 11A and a body portion 11B. The top plate portion 11A of the holder portion 11 has a disk shape and is disposed outside the tire 101.

The body portion 11B has a cylindrical shape, and the axial direction thereof is orthogonal to the top plate portion 11A. The body portion 11B penetrates the side surface 103 of the tire 101. A flow passage 11C extending in the axial direction of the body portion 11 is formed inside the body portion 11B. Further, a screw housing portion 11D is provided on an end portion of the flow passage 11C in the body portion 11B on the top plate portion 11A side. A screw thread is cut outside the body portion 11B, and a screw groove is cut inside the screw housing portion 11D.

The nut 12 is disposed around the outside of the body portion 11B of the holder portion 11. The inside surface of the nut 12 has a screw groove which is cut so as to engage with the screw thread cut on the outside of the body portion 11B of the holder portion 11. The screw thread of the holder portion 11 is engaged with the screw groove of the nut 12, and the side surface 103 of the tire 101 is sandwiched between the top plate portion 11A of the holder portion 11 and the nut 12. The holder portion 11 is fixed to the tire 101 in this manner.

The securing screw 13 is housed and disposed in the screw housing portion 11D of the holder portion 11. The outside surface of the securing screw 13 has a screw thread which is cut so as to engage with the screw groove cut on the inside of the screw housing portion 11D of the holder portion 11. The orifice portion 14 is provided between the securing screw 13 and the bottom surface of the screw housing portion 11D. The screw thread of the securing screw 13 is engaged with the screw groove of the screw housing portion 11D, and the orifice portion 14 is fixed by being pressed against the bottom surface of the screw housing portion 11D by the securing screw 13. Furthermore, the securing screw 13 includes a blowing outlet 13A.

The orifice portion 14 includes a plate-shaped portion 14A, and a small-diameter orifice hole 14B provided in the plate-shaped portion 14A. The orifice hole 14B communicates between the flow passage 11C of the holder unit 11 and the blowing outlet 13A of the securing screw 13. The trace gas that flows into the flow passage 11C passes through the orifice hole 14B, and is blown out to the outside of the tire 101 from the blowing outlet 13A.

A variety type of orifice portions may be used as the orifice portion 14, having a plate-shaped portion 14A with a common external shape, and an orifice hole 14B with a different diameter. By making it possible to exchange the plurality of orifice portions 14 having orifice holes 14B with different diameters, it is possible to adjust the blowing amount when the trace gas is blown out.

As shown in FIG. 1, the determination unit 2 is configured by a PLC 215 and a gas measurement unit 216. The gas measurement unit 216 functions in the same manner as when used in the gas leak inspection device 200. The PLC 215 stores data relating to a fault determination threshold for determining whether or not a fault has occurred in the gas sensors 201. The fault determination threshold may be a concentration of the trace gas, or may be a voltage value. The PLC 215 compares the concentration of the trace gas (or voltage value) sent from the gas measurement unit 216 with the fault determination threshold described above, and determines whether or not a fault has occurred in the gas sensors 201.

Furthermore, the PLC 215 controls the gas supply and discharge unit 203 such that a fixed amount of the trace gas is supplied with respect to the tire 101 when detecting a fault in the gas sensors 201. The fault determination threshold stored in the PLC 215 is determined according to the amount of the trace gas supplied from the gas supply and discharge unit 203 to the tire 101.

Next, a procedure for detecting a fault in the gas sensors 201 using the gas sensor fault detection system will be described. The fault detection of the gas sensors 201 using the gas sensor fault detection system may be performed, for example, at the time of a pre-work inspection performed before inspection work using the gas leak inspection device 200 is started, at the time of an inspection after a changeover, or at the time of confirmation of deterioration of the gas sensors 201.

When detecting a fault in the gas sensors 201, the tire 101 on which the installation jig 10 is installed, is attached to the rotation driver 202A as preparation prior to performing fault detection. The installation jig 10 may be installed at an arbitrary position on the tire 101. Here, for example, when the tire 101 attached to the rotation driver 202A is rotated, the installation jig 10 is installed at a position on the tire 101 that passes directly below the gas sensor 201.

Furthermore, the trace gas can be supplied from the gas supply and discharge unit 203 to the inside of the tire 101 via the lid portion 106, which closes the opening of the tire 101. Next, the trace gas is supplied from the gas supply and discharge unit 203, and the inside of the tire 101 is filled with the trace gas. After the preparation is completed in this manner, fault detection of the gas sensors 201 is performed.

When detecting a fault in the gas sensors 201, the PLC 215 supplies the trace gas from the gas supply and discharge unit 203 and drives the rotation driver 202A. When the trace gas is supplied from the gas supply and discharge unit 203, the trace gas that fills the tire 101 is blown out from the blowing outlet 13A provided in the installation jig 10. When detecting a fault in the gas sensors 201, it is also possible to not perform the supply of the trace gas from the gas supply and discharge unit 203. In this case, the trace gas is blown out from the blowing outlet 13A by the internal pressure of the tire 101. The gas sensors 201 detect the trace gas blown out from the blowing outlet 13A. When the gas sensors 201 detect the trace gas, they output an electric signal (voltage value) corresponding to the concentration of the trace gas as the detection result.

However, when a fault has occurred in a gas sensor 201, then for example even if the trace gas is blown out from the blowing outlet 13A of the installation jig 10, the gas sensor 201 is unable to detect the trace gas, and the gas sensor 201 no longer outputs a voltage value corresponding to the concentration of the trace gas. The gas measurement unit 216 converts the voltage value output from the gas sensor 201 into a concentration of the trace gas, and outputs it to the PLC 215. The PLC 215 compares the concentration of the trace gas sent from the gas measurement unit 216 with the fault determination threshold, and determines whether or not a fault has occurred in the gas sensor 201.

If a fault has not occurred in the gas sensor 201, the gas sensor 201 outputs the voltage value corresponding to the concentration of the trace gas blown out from the blowing outlet 13A of the installation jig 10. Therefore, when the concentration of the trace gas is greater than or equal to the fault determination threshold, it can be determined that a fault has not occurred in the gas sensor 201. Furthermore, if a fault has occurred in the gas sensor 201, the gas sensor 201 outputs a voltage value lower than the voltage value corresponding to the concentration of the trace gas blown out from the blowing outlet 13A of the installation jig 10, such as 0 V. As another example, the gas sensor 201 does not output an electric signal (voltage value). Therefore, when the concentration of the trace gas is less than the fault determination threshold, it can be determined that a fault has occurred in the gas sensor 201.

As described above, in the gas sensor fault detection system using the gas sensor fault detection device 1 of the first embodiment, the installation jig 10 is installed on the tire 101, the trace gas is blown out from the tire 101, and detection is performed by the gas sensors 201. Here, when detecting a fault in the gas sensors 201, the amount and concentration of the trace gas blown out from the tire 101 are known values. Furthermore, because the blowing position of the trace gas is the installation position of the installation jig 10, it is a known position. Here, the tire 101 is capable of being rotated by the rotation driver 202A. Because the rotation driver 202A is controlled by the PLC 215, then even if the tire 101 is rotated, the blowing position of the trace gas is still in a known state. Thus, because the trace gas can be blown out from a known position in a known amount and concentration, then if the gas sensors 201 are operating normally, the concentration of the trace gas detected by the gas sensor 201 should become constant. However, if a fault has occurred in the gas sensors 201, then for example, the detected concentration of the trace gas becomes lower. In the gas sensor fault detection system of the first embodiment, the PLC 215 compares the concentration of the trace gas sent from the gas measurement unit 216 with the fault determination threshold, and determines whether or not a fault has occurred in the gas sensors 201. Therefore, a fault in the gas sensors 201 can be accurately detected.

Furthermore, in the gas sensor fault detection device 1 of the first embodiment, the blowing position of the trace gas is the installation position of the installation jig 10. The installation jig 10 can be at an arbitrary position on the tire 101, for example, at any position on the side surfaces 103 and 104 of the tire 101, or at any position on the ground contact surface 102. Therefore, the blowing position of the trace gas can be easily adjusted. It is possible to support gas leak inspections in anticipation of various cases.

In addition, in the gas sensor fault detection device 1 of the first embodiment, the blowing position of the trace gas is determined by the installation position of the installation jig 10. Because the installation jig 10 is capable of being installed at an arbitrary position of the tire 101, the blowing position of the trace gas can be easily adjusted. Moreover, a small-diameter orifice hole 14B is formed in the orifice portion 14 of the installation jig 10. Consequently, the blowing amount of the trace gas that blows out from the tire 101 can be adjusted, and a minute amount of the trace gas can be blown out from the tire 101. Therefore, the trace gas can be blown out from the tire 101 in a state close to an actual air leak in the tire.

Furthermore, in the gas sensor fault detection device 1 of the first embodiment, the orifice portion 14 in the installation jig 10 can be exchanged for one of a plurality of orifice portions 14 having an orifice hole 14B with a different diameter. As a result, the amount of the trace gas blown out from the installation jig 10 can be adjusted. Further, the installation jig 10 can be installed on a plurality of types of tires having different diameters or sizes. Consequently, the trace gas can be easily blown out from tires (workpieces) having different sizes. Therefore, the gas sensor fault detection device 1 is capable of supporting gas leak inspections in anticipation of various cases, including cases where the size of the workpiece or the leak amount of the trace gas is different.

Second Embodiment

Next, a second embodiment of the present invention will be described with reference to FIG. 4. A gas sensor fault detection device 1B of the second embodiment replaces the configuration in which the installation jig 10 is installed on the tire 101, with the trace gas blowing device 30 shown in FIG. 4.

Figure 4:
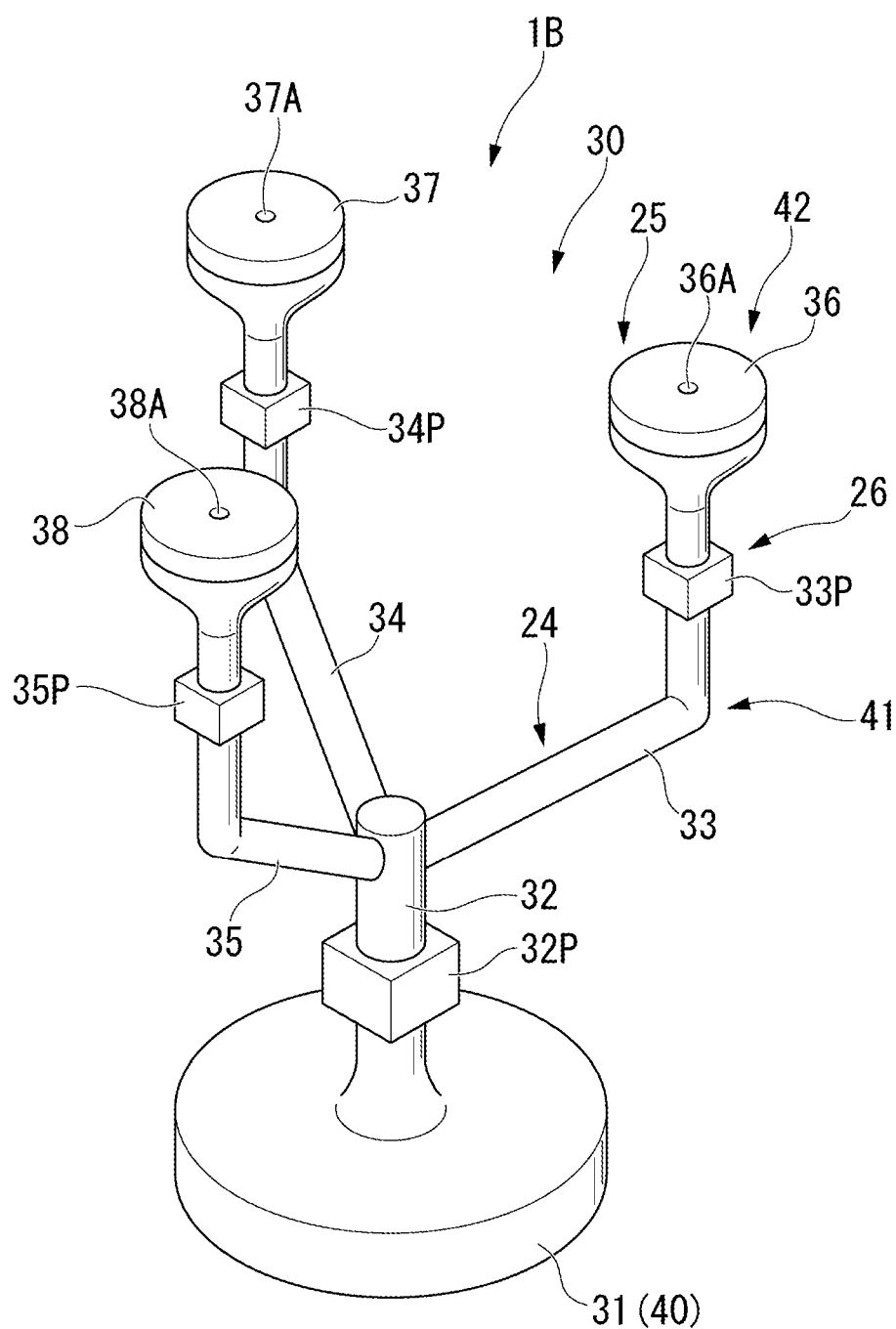
FIG. 4 is a diagram showing another configuration of a gas sensor fault detection device.

As shown in FIG. 4, the trace gas blowing device 30 includes a support 40. The support 40 is configured by a base 31. The base 31 has a disk shape, and is capable of being mounted, for example, on the rotation driver 202A of the gas leak inspection device 200 shown in FIG. 1. The support 40 does not have to be the base 31. For example, the support 40 may be, in addition to a member that is mounted on the rotation driver 202A, a member or the like that is fixed to the rotation driver 202A, or another position.

The gas sensor fault detection device 1B includes a position fixing unit 24, a gas blowing unit 25, and a blowing amount adjustment unit 26. The position fixing unit 24 is configured by a first blowing pipe 33, a second blowing pipe 34 and a third blowing pipe 35. The gas blowing unit 25 is configured by a first blowing head portion 36, a second blowing head portion 37, and a third blowing head portion 38. The blowing amount adjustment unit 26 is configured by a first valve 33P, second valve 34P, and a third valve 35P.

A gas supply pipe holding portion 32 is provided on the base 31. The trace gas is capable of flowing through the inside of the gas supply pipe holding portion 32. An adjustment unit 41 is connected to the gas supply pipe holding portion 32. The adjustment unit 41 is configured by the first blowing pipe 33, the second blowing pipe 34, and the third blowing pipe 35. The trace gas is supplied from the gas supply pipe holding portion 32 to the first blowing pipe 33 to the third blowing pipe 35. The first blowing pipe 33 to the third blowing pipe 35 are configured by, for example, flexible arms.

A gas blowing member 42 is installed on the front end portions of the first blowing pipe 33 to the third blowing pipe 35. The gas blowing member 42 is configured by the first blowing head portion 36 to the third blowing head portion 38. The first blowing head portion 36 to the third blowing head portion 38 are provided with an orifice portion formed with an orifice hole in the same manner as the orifice portion 14 shown in FIG. 3. A first blowing hole 36A, a second blowing hole 37A, and a third blowing hole 38A, from which the trace gas blows out, are provided on the surface of the first blowing head portion 36 to the third blowing head portion 38. The trace gas from the gas supply pipe holding portion 32 is supplied to the first blowing hole 36A to the third blowing hole 38A through the orifice holes. Assuming the tire 101 shown in FIG. 2, the first blowing head portion 36 to the third blowing head portion 38 are disposed at hypothetical gas leak positions where a gas leak in the tire 101 is anticipated to occur. Furthermore, for example, as a result of the first blowing pipe 33 to the third blowing pipe 35 being configured by flexible arms, the arrangement positions and gas blowing angles of the first blowing head portion 36 to the third blowing head portion 38 can be adjusted. The base 31 supports the first blowing head portion 36 to the third blowing head portion 38 via the first blowing pipe 33 to the third blowing pipe 35.

The gas supply pipe holding portion 32 is provided with a lower valve 32P. The first blowing pipe 33 to the third blowing pipe 35 are provided with the first valve 33P to the third valve 35P. By opening the lower valve 32P, the trace gas is capable of passing through the gas supply pipe holding portion 32. On the other hand, by closing the lower valve 32P, the trace gas is unable to pass through the gas supply pipe holding portion 32. By opening the first valve 33P to the third valve 35P, the trace gas is capable of passing through the first blowing pipe 33 to the third blowing pipe 35. On the other hand, by closing the first valve 33P to the third valve 35P, the trace gas is unable to pass through the first blowing pipe 33 to the third blowing pipe 35. The gas supply and discharge unit 203 shown in FIG. 1 is connected to the gas supply pipe holding portion 32. The trace gas is capable of being supplied to the first blowing pipe 33 to the third blowing pipe 35 via the gas supply pipe holding portion 32.

As with the gas sensor fault detection device 1 of the first embodiment, in the gas sensor fault detection device 1B of the second embodiment configured as described above, the trace gas can be blown out from known positions in a known amount and concentration. Therefore, as a result of the PLC 215 comparing the concentrations of the trace gas sent from the gas measurement unit 216 with the fault determination threshold to determine whether or not a fault has occurred in the gas sensors 201, a fault in the gas sensors 201 can be accurately detected.

Furthermore, in the gas sensor fault detection device 1B of the second embodiment, the trace gas is blown out such that the positions on which the gas blowing member 42 of the trace gas blowing device 30 is installed are assumed to be positions in which gas leaks in the tire 101 have occurred. Consequently, the trace gas blown out from a tire can be reproduced without actually using the tire 101. Therefore, a fault in the gas sensors 201 can be easily detected. Moreover, because a fault in the gas sensors 201 is detected without using the tire 101, bursting of the tire 101 during fault detection can be eliminated.

Furthermore, in the gas sensor fault detection device 1B of the second embodiment, the first blowing pipe 33 to the third blowing pipe 35 that configure the adjustment unit 41 are configured by flexible arms. Consequently, by adjusting the shape of the flexible arms, it is possible to easily set the arrangement positions and the gas blowing angles of the first blowing hole 36A to the third blowing hole 38A. Therefore, it is possible to easily reproduce the trace gas blowing out from tires having a variety of sizes and shapes.

Furthermore, in the gas sensor fault detection device 1B of the second embodiment, the gas supply pipe holding portion 32 includes the lower valve 32P, and the first blowing pipe 33 to the third blowing pipe 35 include first valve 33P to the third valve 35P. Consequently, the trace gas blowing out from the first blowing head portion 36 to the third blowing head portion 38 can be collectively adjusted, or also individually adjusted.

In the gas sensor fault detection device 1B of the second embodiment, an example has been described in which the flexible arms of the adjustment unit 41 are used as a configuration that sets the arrangement positions and gas blowing angles of the first blowing hole 36A to the third blowing hole 38A. Here, the flexible arms are manually deformed by an operator. The second embodiment is not limited to such an example. For example, instead of the flexible arms, another configuration such as articulated robot arms may be used as the above configuration. When another configuration is used, the shape may be adjusted by the PCL 215 or the like.

Third Embodiment

Next, a third embodiment of the present invention will be described with reference to FIG. 5A to 5C. As with the gas sensor fault detection device 1B of the second embodiment, a gas sensor fault detection device 1C of the third embodiment replaces the configuration in which the installation jig 10 is installed on the tire 101, with the trace gas blowing device 50 shown in FIG. 5A to 5C.

Figure 5A:
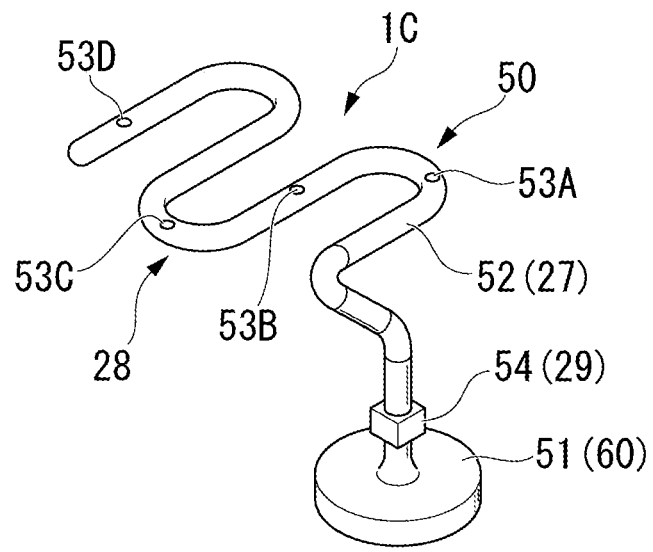
FIG. 5A is a perspective view showing another configuration of a gas sensor fault detection device.
Figure 5B:
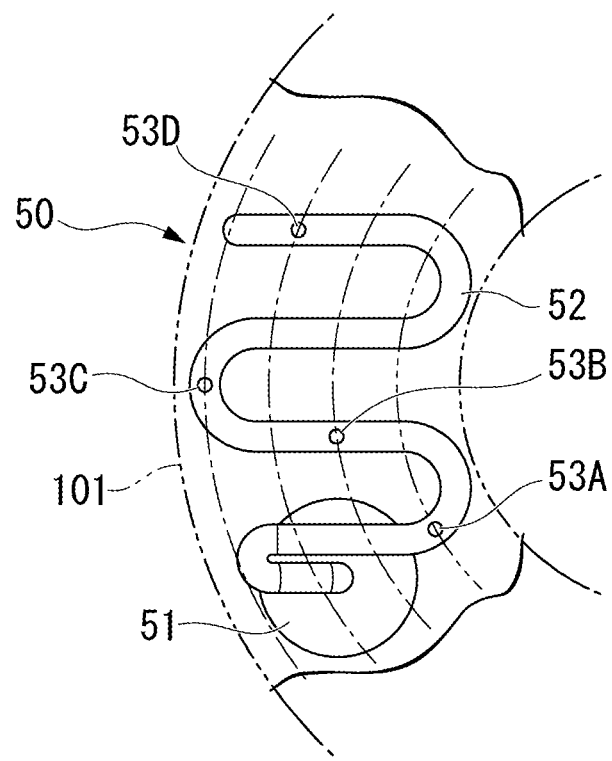
FIG. 5B is a plan view showing the configuration of the gas sensor fault detection device shown in FIG. 5A.

As shown in FIG. 5A, the trace gas blowing device 50 includes a support 60. The support 60 is configured by a base 51. The base 51 has a disk shape, and is capable of being mounted, for example, on the rotation driver 202A of the gas leak inspection device 200 shown in FIG. 1. The support 60 does not have to be the base 51. For example, in addition to a member that is mounted on the rotation driver 202A, it may be a member or the like that is fixed to the rotation driver 202A, or another position.

The gas sensor fault detection device 1C includes a position fixing unit 27, a gas blowing unit 28, and a blowing amount adjustment unit 29. The position fixing unit 27 is configured by a gas blowing pipe 52. The gas blowing unit 28 is configured by a first blowing outlet 53A, a second blowing outlet 53B, a third blowing outlet 53C, and a fourth blowing outlet 53D from which the trace gas is blown out. The blowing amount adjustment unit 29 is configured by a valve 54.

The gas blowing pipe 52 is provided on the base 51. As shown in FIG. 5B, the gas blowing pipe 52 has a meandering shape in plan view. The gas blowing pipe 52 is provided with a plurality of, in this case four, blowing outlets, namely a first gas blowing outlet 53A, a second gas blowing outlet 53B, a third gas blowing outlet 53C, and a fourth blowing outlet 53D. Assuming the tire 101, the first gas blowing outlet 53A to the fourth gas blowing outlet 53D are arranged at positions which are mutually offset in the radial direction of the tire 101.

Figure 5C:
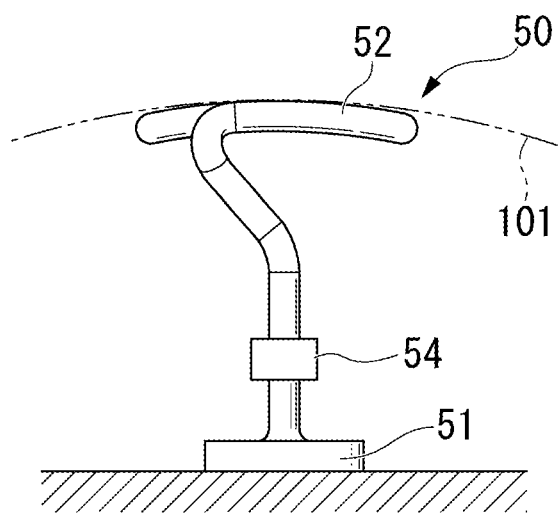
FIG. 5C is a side view showing the configuration of the gas sensor fault detection device shown in FIG. 5A.

As shown in FIG. 5C, the gas blowing pipe 52 is provided in a position that corresponds to the surface of the assumed tire 101. The gas blowing pipe 52 is a rigid pipe, but other forms may be used. For example, as with the first blowing pipe 33 to the third blowing pipe 35 in the second embodiment, the gas blowing pipe 52 may be configured by a flexible arm.

The valve 54 is provided at the end portion of the gas blowing pipe 52 on the base 51 side. By opening the valve 54, the trace gas is capable of passing through the gas blowing pipe 52. On the other hand, by closing the valve 54, the trace gas is unable to pass through the gas blowing pipe 52. The gas supply and discharge unit 203 shown in FIG. 1 is connected to the gas blowing pipe 52, and is capable of supplying the trace gas to the gas blowing pipe 52.

As with the gas sensor fault detection device 1 of the first embodiment, in the gas sensor fault detection device 1C of the third embodiment configured as described above, the trace gas can be blown out from a known position in a known amount and concentration. Therefore, as a result of the PLC 215 comparing the concentrations of the trace gas sent from the gas measurement unit 216 with the fault determination threshold to determine whether or not a fault has occurred in the gas sensors 201, a fault in the gas sensors 201 can accurately detected.

Furthermore, in the gas sensor fault detection device 1C of the third embodiment, the trace gas is blown out such that the positions of the first gas blowing outlet 53A to the fourth gas blowing outlet 53D in the gas blowing pipe 52 of the trace gas blowing device 50 are assumed to be the positions in which gas leaks in the tire 101 have occurred. Consequently, because the trace gas blown out from a tire can be reproduced without actually using the tire 101, a fault in the gas sensors 201 can be easily detected. Moreover, because a fault in the gas sensors 201 is determined without using the tire 101, bursting of the tire 101 during fault determination can be eliminated.

Furthermore, in the gas sensor fault detection device 1C of the third embodiment, the first gas blowing outlet 53A to the fourth gas blowing outlet 53D are arranged at positions which are offset in the radial direction of the assumed tire 101. Consequently, for example, when it is assumed that a fault in the gas sensors 201 is detected in a mode in which the tire 101 is rotated, the gas sensor 201 that has failed can be determined in a short period of time.

Also, in the gas sensor fault detection device 1 of the first embodiment and the gas sensor fault detection device 1B of the second embodiment, when a plurality of gas blowing units are provided, the plurality of gas blowing units may be disposed in positions which are offset in the radial direction of the tire 101, or the assumed tire 101.

In addition, an orifice portion may be provided in the first gas blowing outlet 53A to the fourth gas blowing outlet 53D of the gas sensor fault detection device 1C of the third embodiment. Also, an orifice portion need not be provided in the gas sensor fault detection device 1 of the first embodiment and the gas sensor fault detection device 1B of the second embodiment.

According to a gas sensor fault detection device, a gas sensor fault detection system, and a gas sensor fault detection method of at least one of the embodiments of the present invention, it is possible to support gas leak inspections in anticipation of various cases.

The embodiments of the present invention have been described in detail above with reference to the drawings. However, specific configurations are in no way limited to the embodiments, and include design changes and the like within a scope not departing from the spirit of the present invention.

The present invention may be applied to a gas sensor fault detection device, a gas sensor fault detection system, and a gas sensor fault detection method.

What is claimed is:

1. A gas sensor fault detection device that detects a fault in a gas sensor of a gas leak inspection device, the gas leak inspection device being capable of introducing a gas into an inspection target and of inspecting for a leak of the gas from the inspection target, the gas sensor fault detection device comprising:
    a gas blowing unit from which a gas blows toward a detection area of the gas sensor of the gas leak inspection device, the gas sensor being arranged outside of the inspection target;
    a position fixing unit that fixes the gas blowing unit to a hypothetical gas leak position of the inspection target, the hypothetical gas leak position being a position where the leak of the gas from the inspection target is anticipated to occur when the gas leak inspection device inspects for the leak of the gas; and
    a blowing amount adjustment unit that adjusts an amount of the gas that is blown from the gas blowing unit,
    wherein the gas blowing unit includes a plurality of blowing head portions from which the gas is blown,
    the blowing amount adjustment unit includes a plurality of valves that individually and respectively adjust an amount of the gas that is blown from the plurality of blowing head portions, and
    the gas sensor fault detection device further comprises a support that supports the plurality of blowing head portions.

2. The gas sensor fault detection device according to claim 1, wherein the position fixing unit constitutes a portion of an installation jig installed at the hypothetical gas leak position of the inspection target.

3. The gas sensor fault detection device according to claim 1,
    wherein the gas sensor and the gas blowing unit are movable relative to each other, and
    wherein the gas blown from the gas blowing unit is blown when the gas blowing unit passes a predetermined position.

4. The gas sensor fault detection device according to claim 1, wherein the hypothetical gas leak position is a position of the inspection target near which the gas sensor passes when the inspection target moves.

5. A gas sensor fault detection system comprising:
    a gas leak inspection device that introduces a gas into an inspection target and that inspects for a leak of the gas from the inspection target, the gas leak inspection device comprising a gas sensor arranged outside of the inspection target;
    a gas sensor fault detection device that detects a fault in the gas sensor of the gas leak inspection device, the gas sensor fault detection device comprising:
        a gas blowing unit from which a gas blows toward a detection area of the gas sensor of the gas leak inspection device, the gas sensor being configured to detect the gas blown from the gas blowing unit;
        a position fixing unit that fixes the gas blowing unit to a hypothetical gas leak position of the inspection target, the hypothetical gas leak position being a position where the leak of the gas from the inspection target is anticipated to occur when the gas leak inspection device inspects for the leak of the gas; and a blowing amount adjustment unit that adjusts an amount of the gas that is blown from the gas blowing unit; and a controller programmed to determine whether there is a fault in the gas sensor based on a detection result, from the gas sensor, of the gas blown from the gas blowing unit toward the detection area of the gas sensor, wherein the gas blowing unit includes a plurality of blowing head portions from which the gas is blown, the blowing amount adjustment unit includes a plurality of valves that individually and respectively adjust an amount of the gas that is blown from the plurality of blowing head portions, and the gas sensor fault detection device further comprises a support that supports the plurality of blowing head portions.

6. A gas sensor fault detection method that detects a fault in a gas sensor of a gas leak inspection device, the gas leak inspection device being capable of introducing a gas into an inspection target and of inspecting for a leak of the gas from the inspection target, the gas sensor fault detection method comprising:

fixing a gas blowing unit, which includes a plurality of blowing head portions (i) supported by a support and (ii) from which the gas is blown, to a hypothetical gas leak position of the inspection target, the hypothetical gas leak position being a position where the leak of the gas from the inspection target is anticipated to occur when the gas leak inspection device inspects for the leak of the gas;

causing a gas to be blown from the gas blowing unit toward a detection area of the gas sensor of the gas leak inspection device, the gas sensor being arranged outside of the inspection target and being configured to detect the gas blown from the gas blowing unit;

adjusting, by a blowing amount adjustment unit that includes a plurality of valves that individually and respectively adjust an amount of the gas that is blown from the plurality of blowing head portions, an amount of the gas that is blown from the gas blowing unit; and determining whether there is a fault in the gas sensor based on a detection result, from the gas sensor, of the gas blown from the gas blowing unit toward the detection area of the gas sensor.

* * * * *